US00PP16197P2

(12) United States Plant Patent
Weiskott

(10) Patent No.: US PP16,197 P2
(45) Date of Patent: Jan. 10, 2006

(54) ***MISCANTHUS* PLANT NAMED 'MYSTERIOUS MAIDEN'**

(50) Latin Name: *Miscanthus sinensis*
Varietal Denomination: Mysterious Maiden

(76) Inventor: Jack Weiskott, 229 5th Ave., Greenport, NY (US) 11944

( * ) Notice: Subject to any disclaimer, the term of this patent is extended or adjusted under 35 U.S.C. 154(b) by 64 days.

(21) Appl. No.: 10/972,494

(22) Filed: Oct. 25, 2004

(51) Int. Cl.
*A01H 5/00* (2006.01)

(52) U.S. Cl. ..... Plt./384
(58) Field of Classification Search ..... Plt./384
See application file for complete search history.

*Primary Examiner*—Anne Marie Grunberg
(74) *Attorney, Agent, or Firm*—Penny J. Aguirre

(57) ABSTRACT

A new cultivar of *Miscanthus*, *Miscanthus sinensis* 'Mysterious Maiden', characterized by its gold-banded foliage, narrow leaves, vase-shaped habit and its vigorous growth rate.

2 Drawing Sheets

Botanical classification: *Miscanthus sinensis.*
Varietal denomination: 'Mysterious Maiden'.

BACKGROUND OF THE INVENTION

The present invention relates to a new and distinct cultivar of *Miscanthus sinensis* and will be referred to hereafter by its cultivar name, 'Mysterious Maiden'. 'Mysterious Maiden' represents a new cultivar of Japanese silver grass, a cold hardy, perennial ornamental grass grown for landscape use.

The inventor discovered and selected the new cultivar, 'Mysterious Maiden', in a cultivated area at his nursery in Greenport, N.Y. in summer of 1998. 'Mysterious Maiden' was discovered as a chance seedling that arose in a nursery container of *Rudbeckia maxima.* The parentage of the new cultivar is unknown, however the characteristics of 'Mysterious Maiden' and their presence at the inventor's nursery suggest that *Miscanthus sinensis* 'Gracillimus' (not patented) and *Miscanthus sinensis* 'Zebrinus' (not patented) are likely parents.

The new cultivar 'Mysterious Maiden' was selected for the unique gold banding pattern of its leaf blades combined with its narrow leaves, vase-shaped habit and its vigorous growth rate. In comparison to *Miscanthus sinensis* 'Zebrinus', 'Mysterious Maiden' has narrower leaves, a banding pattern that is comprised of bands that are narrower, more distinct and more frequent and a plant habit that is more vase-shaped. In comparison to *Miscanthus sinensis* 'Gracillimus', 'Mysterious Maiden' is similar in habit but has slightly wider leaves, has a gold banding pattern, blooms earlier, and is shorter in height.

Asexual reproduction of the new cultivar was first accomplished by culm division in Greenport, N.Y. in spring of 1999 by the inventor. The characteristics of this cultivar have been determined to be stable and are reproduced true to type in successive generations.

SUMMARY OF THE INVENTION

The following traits have been repeatedly observed and represent the characteristics of the new cultivar. The new *Miscanthus* has not been observed under all possible environmental conditions. The phenotype may vary somewhat with variations in temperature, day-length, light intensity, soil types, and water and fertility levels without, however, any variance in genotype. The general observations, and descriptions that follow describe plants that were grown outdoors in Greenport, N.Y. for a period of five years. These attributes in combination distinguish 'Mysterious Maiden' from all other selections of *Miscanthus* known to the inventors.

1. The foliage of 'Mysterious Maiden' exhibits a banding pattern of horizontal gold bands on narrow leaves. The banding pattern is retained throughout the growing season.
2. The leave blades of 'Mysterious Maiden' are typically about 4 mm in width tapering to a fine point, 30 to 50% narrower than 'Zebrinus' and about 25% wider than 'Gracillimus'.
3. 'Mysterious Maiden' reaches a height (exclusive of flowerheads) of about 1.5 to 1.8 m (5 to 6 ft), similar in height to 'Zebrinus', shorter than 'Gracillimus' and taller than 'Gold Bar' (U.S. Plant Pat. No. 15,193) and 'Little Zebra' (U.S. Plant Pat. No. 13,008), two other cultivars with gold-banded leaves.
4. The growth habit of 'Mysterious Maiden' is vase-shaped with the leaf blades cascading outward at up to a 45° from the upright culms.
5. 'Mysterious Maiden' blooms in mid to late September in New York, slightly later than 'Zebrinus' and slightly earlier than 'Gracillimus'.

BRIEF DESCRIPTION OF THE DRAWING

The accompanying colored photographs illustrate the overall appearance and distinct characteristics of the new *Miscanthus.*

The photograph in FIG. 1 was taken in late summer and illustrates the overall habit and appearance of 'Mysterious Maiden' in Greenport, N.Y. as grown outdoors for three years after planting from a one-gallon container.

Figure 1:
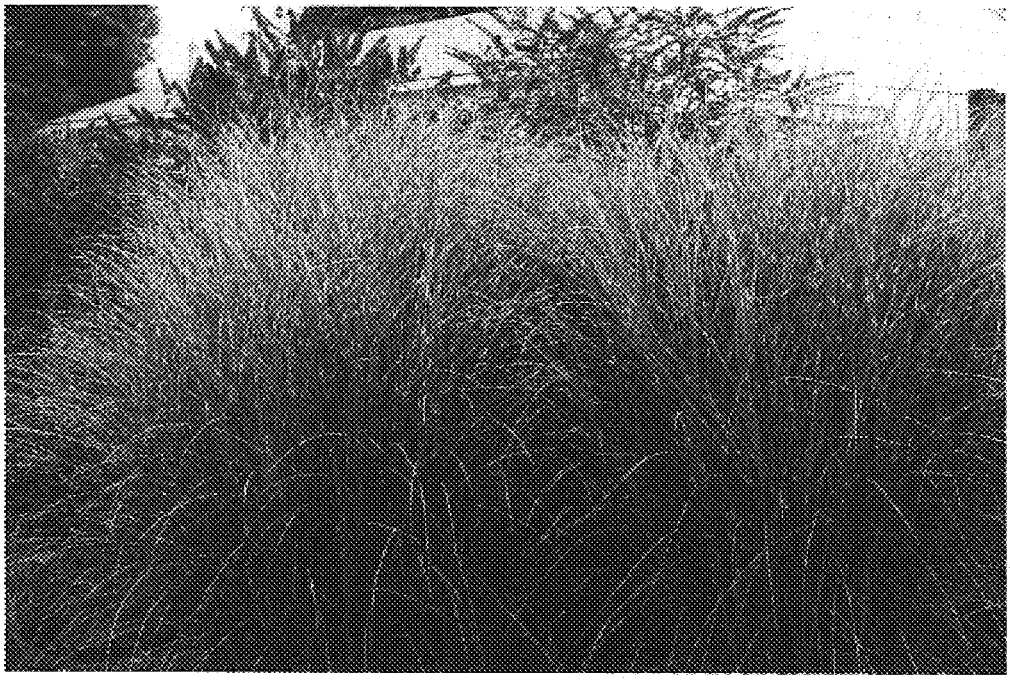
Figure 2:
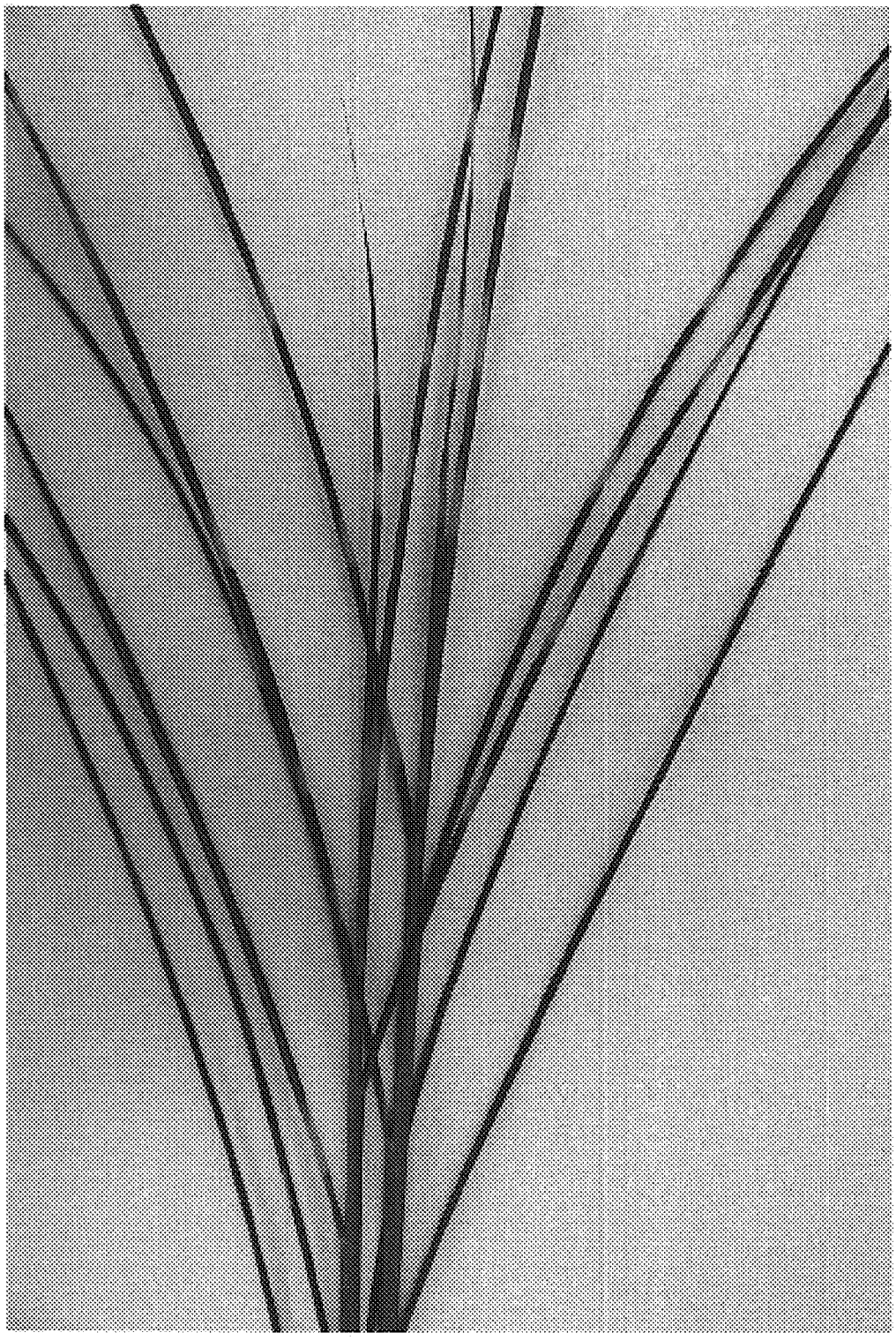

The photograph on FIG. 2 is a close-up view of the banding pattern characteristic of the foliage of 'Mysterious Maiden'.

The colors in the photographs are as close as possible with the photographic and printing technology utilized. The color values cited in the detailed botanical description accurately describe the colors of the new *Miscanthus*.

DETAILED BOTANICAL DESCRIPTION

The general observations and descriptions describe plants that were grown outdoors in Greenport, N.Y. for a period of five years. The detailed botanical description was taken from a plant grown outdoors in garden soil one season from 20-culm division in Plymouth, Minn. The color determinations are in accordance with the 2001 R.H.S. Colour Chart of The Royal Horticultural Society, London, England, except where general color terms of ordinary dictionary significance are used.

Botanical classification: 'Mysterious Maiden' is a cultivar of *Miscanthus sinensis*.

Common name: 'Mysterious Maiden' Japanese silver grass.

Parentage: Naturally occurring chance seedling of *Miscanthus sinensis, Miscanthus sinensis* 'Zebrinus' and *Miscanthus sinensis* 'Gacillimus' are likely parents, but actual parentage is unknown.

General description:

*Blooming period.*—Bloom begins in mid to late September in Greenport, N.Y. and flowers are retained over the winter.

*Plant habit.*—Herbaceous, clump-forming, ornamental grass with an upright culms and leaf blades that cascade in a vase-shaped form.

*Height and spread.*—Reaches a height of about 1.5 to 1.8 m (5 to 6 ft) and a spread at the base of about 1 m (3 ft) with leaves cascading to about 1.8 m (6 ft) in diameter in 5 years of growing time.

*Cold hardiness.*—At least USDA Zone 6, testing in not complete in colder zones.

*Culture.*—Grows best in fertile, moist soil in full sun, tolerates wet soils and light shade in climates with high temperatures, more tolerant to heat and drought than is typical for wider leaved cultivars.

*Diseases and pests.*—No susceptibility or resistance to diseases or pests that affect *Miscanthus* has been observed.

*Root description.*—Fibrous.

Growth and propagation:

*Propagation.*—Culm division, best divided in spring when in active growth.

*Time required for root development from a single division.*—Roots will fully develop in a 6 quart container in 3 to 4 months when grown outdoors under standard summer temperatures and natural lighting in the Northeast U.S.

*Growth rate.*—Vigorous.

Culm (stem) description:

*General.*—Cylindrical, flattened, completely enclosed by leaf sheaths in a fan-like arrangement.

*Culm aspect.*—Rigid and held erect, none are cascading.

*Culm color.*—138B.

*Culm size.*—Up to about 0.6 cm wide, up to 4 to 5 feet in height on mature plants.

*Culm surface.*—Glabrous.

*Internode length.*—About 2 to 6 cm.

*Ligule.*—Membranous, about 1 to 2 mm width and 11B in color with very fine white hairs, encircles the entire culm but glabrous on outer surface of leaves.

Foliage description:

*Leaf shape.*—Linear.

*Leaf division.*—Simple.

*Leaf base.*—Sheathed.

*Leaf apex.*—Acute, tapering to a fine point.

*Leaf aspect.*—Emerging leaves are erect, leaf blades diverge from leaf sheath at ligule at up to a 20° to 40° angle from center of culm. Blades are concave in respect to the culm.

*Leaf venation.*—Parallel, mid rib is raised on upper surface but not conspicuous, color matches the color of the leaf blades on outer surface, 155B on inner surface.

*Leaf margins.*—Entire, with sharp short bristles that are not visually noticeable.

*Leaf persistence.*—Foliage dries but is persistent throughout the winter.

*Leaf attachment.*—Sheathed. Leaf is sheathed from the base of culm and the blade extends out from the culm at a ligule.

*Leaf size.*—Up to about 60 cm in length, typically about 4 mm in width tapering to a point at the apex.

*Leaf surface.*—Glabrous on upper and slightly glaucous on lower surface.

*Leaf number.*—About 9 to 12 leaves per culm on a mature specimen.

*Leaf arrangement.*—Alternate, 2 ranked.

*Leaf surface.*—Glabrous on upper and lower surface, bristles on margin.

*Leaf color and banding description.*—Banding is composed of alternating green and creamy yellow bands. Banding is typically limited to the leaf blade. There is an average of 6 creamy yellow bands per leaf blade measuring 43 cm length. Bands extend the entire width of the leaf blade and height of the bands range from 1 to 3 cm in length, the distance between bands ranges from 2 to 10 cm in length with an average of 5 cm in length. Creamy yellow coloration ranges from 11B to 11C. Banding pattern and colors on the lower surface match those of the upper surface. Green portion of leave is 137A on upper surface and 137B on lower surface.

Flower description:

*General description.*—Compact, fan-shaped panicle terminating from each culm in mid to late September, composed of numerous slender, silky aggregate racemes, cascading to one side, spikelets arranged in two pairs, unequally pedillate.

*Lastingness of inflorescence.*—Panicles are persistent from fall through winter.

*Fragrance.*—None.

*Panicle size.*—Average of 26 cm in length and 8 to 10 cm in width.

*Panicle color.*—Emerges a coppery red over white (effectively 178A, greyed red) and changes to a beige color during plant dormancy (effectively 161A to 161B in color).

*Spikelet description.*—Equal membranaceous glumes, shorter hyaline lemma extending into very fine, flexuous awn extending about 7 mm beyond spikelet, palae small and hyaline.

*Spikelet size.*—About 5 mm in length and 1 mm in width (excluding hairs).

*Spikelet hairs.*—Emerging from the base as a tuft surrounding the base, long, average of 4 mm in length, very fine, 155B in color.

Reproductive organs:

*Androecium.*—Anthers; 3, 2 mm in length and 1 mm in width, 174A in color, basifixed on very fine filament extending about 1.5 mm from spikelet, Pollen; not visible.

*Gynoecium.*—Pistil; 1, 2 plumose stigmas on short, file styles, stigma color is 202A, 1.5 mm in length and 0.3 mm in width, ovary; 1-locular, superior, minute, not easily quantifiable in size and color.

*Caryopsis.*—No caryopsis production was observed.

I claim:

1. A new and distinct cultivar of *Miscanthus* plant named 'Mysterious Maiden' as herein illustrated and described.

* * * * *